(12) United States Patent
Rodeheaver et al.

(10) Patent No.: US 8,871,248 B2
(45) Date of Patent: Oct. 28, 2014

(54) COMPOSITIONS FOR TREATING BIOFILMS AND METHODS FOR USING SAME

(71) Applicant: PluroGen Therapeutics, Inc., Annapolis, MD (US)

(72) Inventors: George Rodeheaver, Charlottesville, VA (US); Adam Katz, Charlottesville, VA (US)

(73) Assignee: PluroGen Therapeutics, Inc., Annapolis, MD (US)

(*) Notice: Subject to any disclaimer, the term of this patent is extended or adjusted under 35 U.S.C. 154(b) by 0 days.

(21) Appl. No.: 13/685,444

(22) Filed: Nov. 26, 2012

(65) Prior Publication Data
US 2013/0101661 A1 Apr. 25, 2013

Related U.S. Application Data

(63) Continuation of application No. 12/033,692, filed on Feb. 19, 2008, now abandoned.

(60) Provisional application No. 60/890,535, filed on Feb. 19, 2007.

(51) Int. Cl.
| | |
|---|---|
| A61L 15/00 | (2006.01) |
| A61L 15/46 | (2006.01) |
| A61L 15/48 | (2006.01) |
| A61K 31/4178 | (2006.01) |
| A61K 31/635 | (2006.01) |
| A61L 15/44 | (2006.01) |
| A61K 47/18 | (2006.01) |
| A01N 59/16 | (2006.01) |
| A01N 43/54 | (2006.01) |
| A61K 47/10 | (2006.01) |
| A61F 13/00 | (2006.01) |

(52) U.S. Cl.
CPC .............. *A61K 47/10* (2013.01); *A61F 13/0063* (2013.01); *A61L 15/46* (2013.01); *A61L 15/48* (2013.01); *A61K 31/4178* (2013.01); *A61K 31/635* (2013.01); *A61L 15/44* (2013.01); *A61F 2013/00638* (2013.01); *A61K 47/18* (2013.01); *A01N 59/16* (2013.01); *A01N 43/54* (2013.01); *A61L 2300/404* (2013.01); *A61L 2300/104* (2013.01)
USPC ............................ 424/445; 514/157; 514/2.4

(58) Field of Classification Search
CPC ... A01N 43/54; A01N 59/16; A01N 2300/00; A01N 25/00; A01N 25/30; A01N 31/02
USPC .................... 424/445; 514/2.4, 157
See application file for complete search history.

(56) References Cited

U.S. PATENT DOCUMENTS

| | | | |
|---|---|---|---|
| 4,906,169 A | 3/1990 | Chien et al. | |
| 4,920,158 A | 4/1990 | Murray et al. | |
| 4,951,622 A | 8/1990 | Takahashi et al. | |
| 5,232,702 A | 8/1993 | Pfister et al. | |
| 5,284,833 A | 2/1994 | McAnalley et al. | |
| 5,298,260 A | 3/1994 | Viegas et al. | |
| 5,326,567 A | 7/1994 | Capelli | |
| 5,393,529 A | 2/1995 | Hoffmann et al. | |
| 5,607,683 A | 3/1997 | Capelli | |
| 5,635,540 A * | 6/1997 | Edlich et al. ............... | 514/772.3 |
| 5,804,213 A | 9/1998 | Rolf | |
| 6,039,965 A | 3/2000 | Donlan et al. | |
| 6,096,225 A | 8/2000 | Yang et al. | |
| 6,096,324 A | 8/2000 | Mansouri | |
| 6,110,381 A | 8/2000 | Wright | |
| 6,149,822 A | 11/2000 | Fabri et al. | |
| 6,201,065 B1 | 3/2001 | Pathak et al. | |
| 6,323,219 B1 | 11/2001 | Costanzo | |
| 6,328,991 B1 | 12/2001 | Myhling | |
| 6,395,189 B1 | 5/2002 | Fabri et al. | |
| 6,399,092 B1 | 6/2002 | Hobson et al. | |
| 6,410,645 B1 | 6/2002 | Pathak et al. | |
| 6,440,437 B1 | 8/2002 | Krzysik et al. | |
| 6,585,961 B1 | 7/2003 | Stockel | |
| 6,723,688 B1 | 4/2004 | Malik et al. | |
| 6,903,243 B1 | 6/2005 | Burton | |
| 6,927,237 B2 | 8/2005 | Hei et al. | |
| 6,977,082 B2 * | 12/2005 | Seitz et al. ..................... | 424/405 |
| 7,083,806 B2 | 8/2006 | Rippon et al. | |
| 7,144,992 B2 | 12/2006 | Madhyastha | |
| 7,976,875 B2 * | 7/2011 | Myntti ........................ | 424/605 |
| 2005/0079147 A1 | 4/2005 | Delaey et al. | |
| 2005/0271604 A1 | 12/2005 | Gestrelius et al. | |
| 2006/0018945 A1 | 1/2006 | Britigan et al. | |

(Continued)

FOREIGN PATENT DOCUMENTS

| | | |
|---|---|---|
| CA | 2599653 | 9/2006 |
| DE | 10238450 A1 | 8/2002 |

(Continued)

OTHER PUBLICATIONS

Ali et al., Investigating the suitability of the Calgary Biofilm device for assessing the antimicrobial efficacy of new agents, 2006, *Biosource Technology* 97:1887-1893.

B Braun Medical AG, "B Braun—Infection Control, Wound Care, Instrument Preparation and Surface Disinfection," Apr. 12, 2006, SPG Media Limited, London, United Kingdom, http://vvww.hospitalmanagement.net/contractors/cleaning/b-braun/.

Ceri et al., The Calgary Device: New Technology for the Rapid Determination of Antibiotic Susceptibilities of Bacterial Biofilms, 1999, *J. Clin. Microbio.* 37(6):1771-1776.

Ceri et al., The MBEC Assay System: multiple equivalent biofilms for antibiotic and biocide susceptibility testing methods, 2001, *Enzymol.* 337:377-385.

(Continued)

*Primary Examiner* — Suzanne Ziska
(74) *Attorney, Agent, or Firm* — Pepper Hamilton LLP

(57) ABSTRACT

Compositions containing a surface active agent and a sublethal amount of an antimicrobial agent and methods for using such compositions are provided herein.

16 Claims, No Drawings

(56) References Cited

U.S. PATENT DOCUMENTS

| | | | | |
|---|---|---|---|---|
| 2006/0052452 | A1* | 3/2006 | Scholz | 514/557 |
| 2006/0246075 | A1 | 11/2006 | Mercken et al. | |
| 2007/0093517 | A1 | 4/2007 | Newton | |
| 2007/0258996 | A1 | 11/2007 | Mookerjee et al. | |
| 2008/0031831 | A1 | 2/2008 | Laali | |
| 2009/0202615 | A1 | 8/2009 | Rodeheaver et al. | |
| 2009/0226541 | A1* | 9/2009 | Scholz et al. | 424/672 |
| 2012/0207700 | A1 | 8/2012 | Koller | |

FOREIGN PATENT DOCUMENTS

| | | |
|---|---|---|
| WO | WO 01/21195 A1 | 3/2001 |
| WO | WO 01/85845 A1 | 11/2001 |
| WO | WO 2004/037115 A2 | 5/2004 |
| WO | WO 2006/099359 A2 | 9/2006 |
| WO | WO 2007/087806 A1 | 8/2007 |
| WO | WO 2008/034138 A1 | 3/2008 |
| WO | WO 2008/103673 A1 | 8/2008 |
| WO | WO 2008/154368 A2 | 12/2008 |
| WO | WO 2010/135449 A1 | 11/2010 |

OTHER PUBLICATIONS

Chandra et al., Antifungal Resistance of Candidal Biofilms Formed on Denture Acrylic in vitro, 2001, *J. Dental Research* 80(3):903-908.

Chiu et al., Evaluation of the in vivo efficacy of topical tobramycin against *Pseudomonas sinonasal* biofilms, 2007, *J. Antimicrobial Chemotherapy* 59(6):1130-1134.

Costerton et al., Microbial biofilms, 1995, *Ann, Rev. Microbiol.* 49:711-745.

Effective Wound Cleansing, Mar. 2007, *The Clinical Services Journal*, Kent, United Kingdom, http://vvww.clinicalservicesjournal.com/Print.aspx?Story=2104.

Extended European Search Report dated Oct. 22, 2012 for EP 08730165.1.

Frank et al., In Vitro Effects of Antimicrobial Agents on Planktonic and Biofilm Forms of *Staphylococcus lugdunensis* Clinical Isolates, 2007, *Antimicrobial Agents and Chemotherapy* 51(3):888-895.

Gennaro, Remington's Pharmaceutical Science, 17$^{th}$ ed., Mack Publishing Company, Easton, PA 1985 (TOC).

Goto et al., In Vitro Bactericidal Activities of Beta-Lactamases, Amikacin, and Fluoroquinolones Against *Pseudomonas aeruginose* Biofilm in Artificial Urine, 1999, *Urology* 53(5):1058-1062.

Horrocks, Prontosan Wound Irrigation and Gel: Management of Chronic Wounds, *British Journal of Nursing*, vol. 15, Iss. 22, Dec. 14, 2006, pp. 1222-1228, London, United Kingdom, http://www.internurse.com/cgi-bin/go.pl/library/article.cgi?uid=22559; article=BJN_15_22_1222_1228.

International Search Report and Written Opinion of the International Searching Authority, Jun. 27, 2008, from counterpart foreign application PCT/US2008/054306, International Filing Date Feb. 19, 2008.

International Search Report and Written Opinion of the International Searching Authority, Jul. 13, 2010, from counterpart foreign application PCT/US2008/035440, International Filing Date May 19, 2010.

Marsh, Plaque as a biofilm: pharmacological principles of drug delivery and action in the sub- and supragingival environment, 2003, *Oral Diseases* 9(1):16-22.

Melchior et al., Comparative Assessment of the Antimicrobial Susceptibility of *Staphylococcus aureus* Isolates from Bovine Mastitis in Biofilm Versus Planktonic Culture, 2006, *J. Veterinary Medicine Series B* 53(7):326-332.

Nickel et al., Tobramycin resistance of *Pseudomonas aeruginose* cells growing as a biofilm on urinary catheter material, 1985, *Antimicrob, Agents Chemother.* 27(4):619-624.

Olson et al., Biofilm Bacteria: formation and comparative susceptibility to antibiotics, 2002, *Canadian J. Veterinary Research* 66:86-92.

Paulson, Efficacy of preoperative antimicrobial skin preparation solutions on biofilm bacteria, 2005, *AORN Journal* 81(3):503-506.

Rodeheaver et al., Pharmacokinetics of a New Skin Wound Cleanser, *American Journal of Surgery*, (Jul. 1, 1976), 132(1):67-74.

Sedlacek et al., Antibiotic resistance in an in vitro subgingival biofilm model, 2007, *Oral Microbiology & Immunology* 22(5):333-339.

Surdeau et al., Sensitivity of bacterial biofilms and planktonic cells to a new antimicrobial agent, Oxsil 320N, 2006, *J. Hospital Infection* 62(4):487-493.

Wesenberg-Ward et al., Adhesion and Biofilm Formation of *Candida albicans* on Native and Pluronic-treated Polystyrene, Biofilms, (Jan. 1, 2005), 2(1):63-71 (Abstract).

Yousef et al., Inhibition of Bacterial Adherence and Biofilm on Contact Lenses, *Egypt. J. Biomed. Sci.* (1998), 1, 79-94 (Abstract).

Nickel, et al., Bacterial biofilms and catheters: A key to understanding bacterial strategies in catheter-associated urinary tract infection, Sep./Oct. 1992, Can J. Infect Dis vol. 3 No. 5.

Baskaran et al. "Poloxamer-188 Improves Capillary Blood Flow and Tissue Viability in a cutaneous burn wound" Apr. 4, 2001, *J. of Surgical Res.* 101:56-61.

Supplemental European Search Report dated Jan. 23, 2013, for corresponding application EP 10778342.

Satas Handbook of Pressure Sensitive Adhesive Technology, 2$^{nd}$ Edition (1989) Van Nostrand Reinhold, New York, Chapter 1.

Birchenough, S.A.; et al. "Topical poloxamer-188 improves blood flow following thermal injury in rat mesenteric microvasculature." Annals of Plastic Surgery, 2008, 60, 584-588.

* cited by examiner

COMPOSITIONS FOR TREATING BIOFILMS AND METHODS FOR USING SAME

CROSS-REFERENCE TO RELATED APPLICATIONS

This application is a continuation of U.S. patent application Ser. No. 12/033,692 entitled "Compositions For Treating Biofilms And Methods For Using Same," filed Feb. 19, 2008 which claims priority to and benefit of U.S. Provisional Application No. 60/890,535 entitled "Treating Biofilm with Surfactant Compositions" filed on Feb. 19, 2007 the entire contents of which are hereby incorporated by reference in their entireties.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

1. Field of Invention
Not Applicable
2. Description of Related Art

Bacteria and fungi form biofilms under certain conditions. When a group of bacteria or fungi accumulate on a surface and reach a particular cell density, they begin to secrete a polymeric substance that consists of polysaccharides, proteins and DNA and form a matrix in which the bacterial or fungal cells are entrenched. The multi-cellular aggregates or biofilms allow for individual bacterial or fungal cells or colonies of bacterial or fungal cells to exhibit coordinated behavior and confer upon the microorganism advantages including, for example, resistance to antibiotics and host immune systems. More specifically, biofilms are structured to allow respiration and fluid and nutrient exchange while preventing access of host immune cells such as phagocytes and preventing inhibitory or lytic concentrations of antimicrobials from reaching the microorganisms. As a result of these properties, infections that result from biofilm formation are notoriously difficult to eradicate and require the use of high concentrations of antimicrobial agents, removal of tissue, debridement of affected tissues and combination of these treatments.

Biofilm formation appears to be governed by secretion and detection of autoinducer molecules in a process referred to as "quorum sensing." By this process, as quorum sensing autoinducer molecules begin to accumulate in the area surrounding the microorganisms, the microorganisms begin to undergo a number of physiological changes which allow for formation of the extracellular biofilm. For example, as a result of quorum sensing autoinducer accumulation, the microorganisms may begin surface attachment, extracellular polymer production, biosurfactant production, sporulation, bioluminescence and secretion of nutrient sequesteration molecules and virulence factors among other effects resulting in biofilm formation.

Because of the properties provided by the polymeric matrix and the physiological changes exhibited by microorganisms in a biofilm, microorganisms in a biofilm are typically less susceptible to antibiotics, antimicrobials and biocides. In some cases, bacteria in a biofilm can be up to 4,000 times more resistant (i.e., less susceptible) than the same organism in a free-floating (planktonic) state. Comparisons of minimum inhibitory concentration (MIC) which describes the amount of an active agent delivered to planktonic microorganisms necessary to inhibit biofilm formation and minimum biofilm eradication concentration (MBEC) which describes the minimum concentration of an active agent delivered to a biofilm necessary to inhibit or eradicate biofilm growth illustrate the differences in susceptibility from the planktonic bacteria to those in a biofilm and show that biofilm forming bacteria are much less susceptible to antimicrobial agents at standard therapeutic concentrations. Moreover, using an MIC concentration of antibiotic in a biofilm infection can inadvertently expose the biofilm to a sub-lethal dose of antibiotics which may increase the likelihood of the exposed biofilm forming microorganisms developing resistance to the antimicrobial agent which can have grave consequences for effective treatment of the biofilm.

BRIEF SUMMARY OF THE INVENTION

Embodiments of the invention described herein are directed to a method for treating a microbial biofilm on a patient including the steps of contacting the microbial biofilm with a composition comprising a surface active agent and a sub-lethal amount of an antimicrobial agent.

In some embodiments, the antimicrobial agent may be an antibacterial, antifungal, antiviral or combinations thereof, and in others, the antimicrobial agent may be furaltadone, furazolium chloride, nifuradene, nifuratel, nifurfoline, nifurpirinol, nifurprazine, nifurtoinol, nitrofurantoin, furazolidone, 2-(methoxymethyl)-5-nitrofuran, nidroxyzone, nifuroxime, nifurazide, nitrofurazone, nystatin, polymyxin, silver sulfadiazine, nanocrystalline silver, ionic silver, honey, iodine, benzalkonium chloride, alcohol, hydrogen peroxide, chlorhexidine or combinations thereof. In certain embodiments, a sub-lethal amount of an antimicrobial agent may be a standard therapeutically effective amount. In particular embodiments, the antimicrobial agent may be silver sulfadiazine and the sub-lethal amount may be less than about 1% by weight of the composition, less than about 0.95% by weight of the composition, or less than about 0.75% by weight of the composition.

The surface active agent of embodiments may be a poloxamer, meroxapol, poloxamine or combinations thereof. In some embodiments, the surface active agent may be a poloxamer 127, poloxamer 188, poloxamer 237, poloxamer 335, poloxamer 407 or combinations thereof, and in certain embodiments, the surface active agent may be poloxamer 188.

The step of contacting the microbial biofilm in various embodiments may include applying the composition to a wound. In some embodiments, the step of contacting the microbial biofilm may include administering the composition topically, and in particular embodiments, administering the composition topically may be selected from administering by hand, administering by an extruder, spray delivery, applying a dressing including the composition or combinations thereof. In other embodiments, the step of contacting the microbial biofilm may include contacting tissue from the patient that is outside the patient, and in still other embodiments, the step of contacting may include applying the composition to a dressing prior to applying the dressing to the patient.

In some embodiments, the patient may be afflicted with an injury, and in certain embodiments, the injury may be a burn, abrasion, cut, scrape, denuding tissue injury or combinations thereof. In other embodiments, the patient may be afflicted with a chronic wound, and in particular embodiments, the chronic wound may be a venous ulcer, diabetic ulcer, arterial ulcer, pressure ulcer, radiation ulcer, traumatic wound, non-healing wound or combinations thereof.

Embodiments of the invention also include a method for preventing a microbial biofilm on a patient including the steps of administering a composition comprising a surface active agent and a sub-lethal amount of an antimicrobial agent to an injury.

In some embodiments, the antimicrobial agent may be an antibacterial, antifungal, antiviral or combinations thereof, and in others, the antimicrobial agent may be furaltadone, furazolium chloride, nifuradene, nifuratel, nifurfoline, nifurpirinol, nifurprazine, nifurtoinol, nitrofurantoin, furazolidone, 2-(methoxymethyl)-5-nitrofuran, nidroxyzone, nifuroxime, nifurazide, nitrofurazone, nystatin, polymyxin, silver sulfadiazine, nanocrystalline silver, ionic silver, honey, iodine, benzalkonium chloride, alcohol, hydrogen peroxide, chlorhexidine or combinations thereof. In particular embodiments, the antimicrobial agent may be silver sulfadiazine and the sub-lethal amount may be less than about 1% by weight of the composition, less than about 0.95% by weight of the composition, or less than about 0.75% by weight of the composition.

The surface active agent of embodiments may be a poloxamer, meroxapol, poloxamine or combinations thereof. In some embodiments, the surface active agent may be a poloxamer 127, poloxamer 188, poloxamer 237, poloxamer 335, poloxamer 407 or combinations thereof, and in certain embodiments, the surface active agent may be poloxamer 188.

The step of contacting the microbial biofilm in various embodiments may include applying the composition to a wound. In some embodiments, the step of contacting the microbial biofilm may include administering the composition topically, and in particular embodiments, administering the composition topically may be selected from administering by hand, administering by an extruder, spray delivery, applying a dressing including the composition or combinations thereof. In other embodiments, the step of contacting the microbial biofilm may include contacting tissue from the patient that is outside the patient, and in still other embodiments, the step of contacting may include applying the composition to a dressing prior to applying the dressing to the patient.

In particular embodiments, the composition may be administered while biofilm forming pathogens are in a planktonic state.

Further embodiments of the invention include a method for treating or preventing a microbial biofilm in a patient including the steps of administering a first composition comprising a surface active agent to an injury wherein the first composition does not contain an antimicrobial agent and administering a second composition comprising a surface active agent and a sub-lethal amount of an antimicrobial agent to the injury. In certain embodiments, the first composition may be administered before the second composition, and in some embodiments, the second composition may be applied to a dressing prior to its administration.

In various embodiments, the antimicrobial agent of the second composition may be an antibacterial, an antifungal, an antiviral or a combination thereof, and in some embodiments, the antimicrobial agent of the second composition may be furaltadone, furazolium chloride, nifuradene, nifuratel, nifurfoline, nifurpirinol, nifurprazine, nifurtoinol, nitrofurantoin, furazolidone, 2-(methoxymethyl)-5-nitrofuran, nidroxyzone, nifuroxime, nifurazide, nitrofurazone, nystatin, polymyxin, silver sulfadiazine silver salts, nanocrystalline silver, ionic silver, iodine, benzalkonium chloride, alcohol, hydrogen peroxide, chlorhexidine or combinations thereof. In particular embodiments, the antimicrobial agent may be silver sulfadiazine and the sub-lethal amount may be less than about 1% by weight of the composition, less than about 0.95% by weight of the composition, or less than about 0.75% by weight of the composition.

The surface active agents in the first and second composition of various embodiments may be surfactants. In some embodiments, the surface active agents in the first and second compositions may independently be poloxamer 127, poloxamer 188, poloxamer 237, poloxamer 335, poloxamer 407 or combinations thereof. In particular embodiments, the surface active agents in the first and second compositions may be the same, and in at least one embodiment, surface active agents in the first and second compositions may be poloxamer 188.

Embodiments also include a composition for treating or preventing a microbial biofilm including a surface active agent and a sub-lethal amount of an antimicrobial agent.

In some embodiments, the antimicrobial agent may be an antibacterial, antifungal, antiviral or combinations thereof, and in others, the antimicrobial agent may be furaltadone, furazolium chloride, nifuradene, nifuratel, nifurfoline, nifurpirinol, nifurprazine, nifurtoinol, nitrofurantoin, furazolidone, 2-(methoxymethyl)-5-nitrofuran, nidroxyzone, nifuroxime, nifurazide, nitrofurazone, nystatin, polymyxin, silver sulfadiazine, nanocrystalline silver, ionic silver, honey, iodine, benzalkonium chloride, alcohol, hydrogen peroxide, chlorhexidine or combinations thereof. In certain embodiments, a sub-lethal amount of an antimicrobial agent may a standard therapeutically effective amount. In particular embodiments, the antimicrobial agent may be silver sulfadiazine and the sub-lethal amount may be less than about 1% by weight of the composition, less than about 0.95% by weight of the composition, or less than about 0.75% by weight of the composition.

The surface active agent of various embodiments may be a poloxamer, meroxapol, poloxamine or combinations thereof. In embodiments in which the surface active agent is a poloxamer, the poloxamer may be a poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 and poloxamer 407 or combinations thereof. Agent is a copolymer selected from poloxamer 127, poloxamer 188, poloxamer 237, poloxamer 335, poloxamer 407 or combinations thereof. In particular embodiments, the surface active agent may be poloxamer 188. In embodiments in which the surface active agent is a meroxapol, the meroxapol may be a meroxapol 105, meroxapol 108, meroxapol 171, meroxapol 172, meroxapol 174, meroxapol 178, meroxapol 251, meroxapol 252, meroxapol 254, meroxapol 258, meroxapol 311, meroxapol 312, meroxapol 314 or combinations thereof. In embodiments in which the surface active agent is a poloxamine, the poloxamine may be a poloxamine 304, poloxamine 504, poloxamine 701, poloxamine 702, poloxamine 704, poloxamine 707, poloxamine 901, poloxamine 904, poloxamine 908, poloxamine 1101, poloxamine 1102, poloxamine 1104, poloxamine 1301, poloxamine 1302, poloxamine 1304, poloxamine 1307, poloxamine 1501, poloxamine 1502, poloxamine 1504, poloxamine 1508 or combinations thereof.

In some embodiments, the composition may include one or more secondary active agents, and in others, the composition may include one or more additives. In particular embodiments, the composition may further include a solvent.

Embodiments of the invention also include a dressing for treating or preventing a microbial biofilm including a first composition layer comprising a surface active agent wherein the first gel layer does not include an antimicrobial agent, a second composition layer comprising a surface active agent and a sub-lethal amount of an antimicrobial agent, and a dressing material supporting said first and second composition layers. In some such embodiments, the second composition layer may be located between the first composition layer and the dressing material.

In some embodiments, the antimicrobial agent may be an antibacterial, antifungal, antiviral or combinations thereof, and in others, the antimicrobial agent may be furaltadone, furazolium chloride, nifuradene, nifuratel, nifurfoline, nifurpirinol, nifurprazine, nifurtoinol, nitrofurantoin, furazolidone, 2-(methoxymethyl)-5-nitrofuran, nidroxyzone, nifuroxime, nifurazide, nitrofurazone, nystatin, polymyxin, silver sulfadiazine, nanocrystalline silver, ionic silver, honey, iodine, benzalkonium chloride, alcohol, hydrogen peroxide, chlorhexidine or combinations thereof. In particular embodiments, the antimicrobial agent may be silver sulfadiazine and the sub-lethal amount may be less than about 1% by weight of the composition, less than about 0.95% by weight of the composition, or less than about 0.75% by weight of the composition.

The surface active agent of embodiments may be a poloxamer, meroxapol, poloxamine or combinations thereof. In some embodiments, the surface active agent may be a poloxamer 127, poloxamer 188, poloxamer 237, poloxamer 335, poloxamer 407 or combinations thereof, and in certain embodiments, the surface active agent may be poloxamer 188.

In some embodiments, the surface active agent in the first and second compositions may be the same. In other embodiments, the dressing may further include a spacer material layer between said first and second composition layers. The spacer material of such embodiments may fully or partially lose integrity upon application of the dressing to a patient. In particular embodiments, the second composition layer may impregnate the dressing material.

Other embodiments of the invention also include a method for preventing a microbial biofilm on a patient including the steps of administering a composition including a surface active agent and a sub-lethal amount of an antimicrobial agent to a wound prior to infection. Still other embodiments of the invention include a method for preventing a microbial biofilm on a patient including the steps of administering a composition including a surface active agent and a sub-lethal amount of an antimicrobial agent to a wound while biofilm forming bacteria are in a planktonic state. Yet other embodiments of the invention include a method for preventing a microbial biofilm on a patient including the steps of administering a composition comprising a surface active agent and a sub-lethal amount of an antimicrobial agent to a wound prior to infection wherein the composition is administered within 10 hours of the injury. Further embodiments of the invention include a method for treating or preventing a microbial biofilm on a patient including the steps of administering a composition comprising a surface active agent to a wound.

DESCRIPTION OF DRAWINGS

Not Applicable

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must be noted that, as used herein, and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes instances where the event occurs and instances where it does not.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by injection, infusion, or by either method in combination with other known techniques. Such combination techniques include heating, radiation and ultrasound.

The terms "treat," "treating" or treatment" generally mean the exposure of a living organism to one or more physical, chemical or psychological entities or stimuli that may prevent, improve or ameliorate a diseased state. These terms are also meant to encompass exposing an inanimate object (e.g., biomaterial) to physical or chemical entities or stimuli that may enhance the object's capacity to alter a disease process in living organisms which is contacted by the object. For example, treating a biomaterial may include applying a composition to a surface of a biomaterial to enhance resistance to biofilm development, dissolve an existing biofilm and/or deliver a therapeutic to the biomaterials. Biomaterial treatment may encompass treating an entry site for catheters in the body of a patient which allow access of the catheter to, for example, blood vessels, body cavities, cerebrospinal space and the like.

The term "indication", as used herein, refers to a medical condition or symptoms associated with a medical condition, such as biofilm infection. For example, redness and swelling of tissue surrounding an injury may be an indication of subject in a diseased state.

The term "target", as used herein, refers to the material for which deactivation, rupture, disruption or destruction is desired. For example, infectious microorganisms or biofilms may be considered undesirable material in an injured subject and may be a target for therapy.

Generally speaking, the term "tissue" refers to any aggregation of similarly specialized cells which are united in the performance of a particular function. For example, skin may be considered a tissue.

The term "diseased tissue", as used herein, refers to tissue or cells associated with an injury that has become infected with microorganisms, and in particular, microorganisms capable of forming a biofilm or tissue on which a biofilm has formed.

The term "improves" is used to convey that the present invention changes either the appearance, form, characteristics and/or the physical attributes of the tissue to which it is being provided, applied or administered. For example, eradication of the bio film would improve the indications of the injury.

As used herein, the term "therapeutic" means an agent utilized to treat, combat, ameliorate, prevent or improve an unwanted condition or disease of a patient.

A "therapeutically effective amount" or "effective amount" of a composition as used herein is a predetermined amount calculated to achieve the desired effect. For example, a "therapeutically effective amount" of a composition of the invention may achieve one or more of preventing formation of a biofilm, disrupting preformed biofilm and/or enabling contact of one or more therapeutic agents with the microorganism responsible for the biofilm or enabling augmentation of the state of the tissue underlying the biofilm so as to ameliorate the disease state.

A "biofilm" as used herein describes an aggregate of microorganisms that exhibit cooperative behavior such as, for example, secretion of a polymeric matrix that protects the microorganisms from attack by the host immune system.

By "biomaterial" is meant, a non-drug material that can be used to treat, enhance, or replace any tissue, organ, or function in an organism.

A "surface active agent" or "surfactant," as used herein, may refer to a substance that is capable of reducing the surface tension of a material.

Embodiments of the invention presented herein are generally directed to compositions for use in preventing the formation of biofilms and treating biofilms that have formed, methods for using such compositions and materials including such compositions such as, for example, wound dressings, surgical equipment and syringes. Embodiments of the invention are directed to treating biofilms both living and non-living objects using the compositions of the invention. Some embodiments are directed to compositions and methods useful for the treatment of a patient, living tissue or biomaterial. Compositions used in such embodiments may be referred to as "pharmaceutical compositions" which generally refers to a composition that is meant for application on or in a patient, living tissue or a biomaterial. Similar compositions, even those having the same makeup, may be useful in methods for treating biofilms on objects that are not living or utilized in the treatment of a living being which are also encompassed by the invention described herein.

In various embodiments, the composition of the invention may at least include a surface active agent and a sub-lethal amount or dose of an antimicrobial agent. Surface active agents are well known in the art, and suitable surface active agents for preparing the compositions of the invention are not particularly limiting. For example, anionic, cationic or non-ionic surface active agents may be used individually or in combination. In some embodiments, non-ionic surface active agents based on a polyol and including alkylene oxide units such as ethylene oxide and propylene oxide may be used.

Such non-ionic surface active agents include, but are not limited to, glycerol stearate/polyethylene glycol stearate copolymers marketed under the trade name, ARLACEL™ and sorbitan stearate/sugar cocoate copolymers marketed under the trade name ARLATONE™. In other embodiments, the surface active agent may be a copolymer, such as, a poloxamer, meroxapol, and poloxamine.

Poloxamers are well known in the art and generally refer to a class of non-ionic di-block or tri-block copolymers having a central hydrophobic chain of polyoxypropylene flanked by hydrophilic chains of polyoxyethylene. An exemplary tri-block poloxamer may be of general formula:

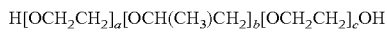

where a, b and c are an integer and reflect the number of ethylene oxide and propylene oxide monomers in each block. The length of each polymer block may vary and may provide poloxamers with different properties, and poloxamers are available in various grades. In general, poloxamers are named using three digits, the first two digits×100 give the approximate molecular mass of the polyoxypropylene core and the last digit×10 gives the percentage polyoxyethylene content in the poloxamer. For example, poloxamer 188 would be expected to contain a polyoxypropylene core of 1800 g/mol and a polyethylene content of approximately 80%. Exemplary poloxamers useful in embodiments of the invention may include, but are not limited to, poloxamers 101, 105, 105 benzoate, 108, 122, 123, 124, 181, 182, 182 dibenzoate, 183, 184, 185, 188, 212, 215, 217, 231, 234, 235, 237, 238, 282, 284, 288, 331, 333, 334, 335, 338, 401, 402, 403 and 407.

Meroxapols are well known in the art and generally refer to a class of nonionic di-block or tri-block copolymers having a central hydrophilic chain of polyoxyethylene flanked by hydrophobic chains of polyoxypropylene. An exemplary tri-block meroxapol may be of general formula:

where a, b and c are an integer and reflect the number of ethylene oxide, and propylene oxide monomers in each block. The length of each polymer block may vary and may provide meroxapols with different properties. Meroxapols are available in various grades, and are named using the system described above for poloxamers. Examples of meroxapols useful in embodiments of the invention include, but are not limited to, meroxapols 105, 108, 171, 172, 174, 178, 251, 252, 254, 258, 311, 312 and 314.

Poloxamines are well known in the art and generally refer to a class of nonionic tri-block copolymers having a central ethylene diamine flanked on either side by polyoxyethylene-polyoxypropylene block copolymers. Such compounds conform to general formula:

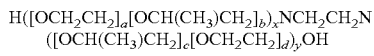

where a, b, c and d are an integer and reflect the number of ethylene oxide and propylene oxide monomers in each polyoxyethylene-polyoxypropylene copolymer block and x and y are integers and reflect the number of polyoxyethylene-polyoxypropylene copolymer blocks in each block. Poloxamines are available in different grades and are named using the system described above for poloxamers. Examples of poloxamines useful in embodiments of the invention include, but are not limited to poloxamines 304, 504, 701, 702, 704, 707, 901, 904, 908, 1101, 1102, 1104, 1301, 1302, 1304, 1307, 1501, 1502, 1504 and 1508.

The number average molecular weight ($M_n$) of surface active agents, and particularly copolymer surface active agents of embodiments may vary and may be, for example, from about 600 to about 20,000, in some embodiments from about 600 to about 10,000, and in other embodiments, from about 1,000 to about 9,000. In particular embodiments, the $M_n$ may be from about 5,000 to about 8,500. The weight of hydrophobic groups may also vary and may be from about 45% to about 95% by weight of the copolymer.

The surface active agent of embodiments may be hydrated by mixing a suitable dry formulation of a surface active agent with a solvent such as, for example, water. Surface active agents may be hydrated by any method known in the art. For example, in some embodiments a surface active agent including a copolymer (e.g., a poloxamer) can be hydrated by cooling a mixture of the copolymer and water to an appropriate temperature such as, for example, about 0° F. to about 50° F. for at least 4 hours. The ratio of surface active agent to solvent may vary among embodiments and may be, for example, about 0.01% to about 99.99% w/w, about 20% to about 90% w/w, about 30% to about 80% w/w and about 40% to about 70% w/w. In particular embodiments the ratio of surface active agent to water may be 1:1 or about 50% w/w. Such embodiments are described in greater detail in U.S. Pat. No. 5,635,540, the contents of which are incorporated herein by reference in its entirety.

Embodiments of the invention include the use of a surface active agent such as those described above to treat or eradicate a biofilm or planktonic biofilm forming microorganisms. In such embodiments, a composition including a surface active agent may be applied to a surface or wound where biofilm exists or where planktonic biofilm forming microorganism may be present and there is a high likelihood of a biofilm forming. The composition may reduce or eliminate an existing biofilm or inhibit the growth of or eradicate biofilm forming microorganisms thereby reducing or eliminating the formation a biofilm. Such compositions may be applied to a wound on a patient or applied to a surface, such as, an operating table or surgical instruments with similar efficacy.

In certain embodiments, the surface active agent composition may further include one or more therapeutic agents (e.g., 2, 3, or 4 therapeutic agents may be added to a surface active agent). In general, a therapeutic agent may be added to a surface active agent after the surface active agent has been hydrated. However, in some embodiments, a dry surface active agent may be mixed with a dry therapeutic agent and the surface active agent may be hydrated following such mixing. In other embodiments, a dry mixture of surface active agent and therapeutic agent may be prepared and stored for a period of time before the surface active agent is hydrated. Any therapeutic agent known in the art may be mixed with the surface active agent to prepare a composition encompassed by the invention. For example, useful therapeutic agents may include, but are not limited to, antimicrobials, steroids (e.g., hydrocortisone, triamcinolone), pain medications (e.g., aspirin, an NSAID, and a local anesthetic), anti-inflammatory agents, biological cells and biological agents of various types and combinations thereof.

In certain embodiments, the therapeutic agent may be an antimicrobial agent. Antimicrobial agents are well known and utilized in the art and include antibacterial, antifungal, and antiviral agents. Examples of antimicrobials useful in embodiments of the invention include, but are not limited to, silver sulfadiazine, nanocrystalline silver, ionic silver, nystatin, nystatin/triamcinolone, bacitracin, nitrofurazone, nitrofurantoin, polymyxins (e.g., colistin, surfactin, polymyxin E and polymyxin B), doxycycline, natural and synthetic antimicrobial peptides and combinations of agents. Antimicrobials of embodiments may also include topical antimicrobials (i.e., antiseptics), for example, silver salts, iodine, benzalkonium chloride, alcohol, hydrogen peroxide, chlorhexidine, honey and the like.

As described above, the polymer matrix formed between microorganisms forms a barrier to many antimicrobial agents. Therefore, treatment of biofilms and biofilm forming microorganisms generally requires one or more doses of an antimicrobial agent that is often several times greater than the lethal dosage required to treat individual microorganisms that do not form biofilms or planktonic biofilm forming microorganisms. Moreover, it has been reported that sub-inhibitory concentrations of antimicrobial agents may induce biofilm formation (see, for example, Frank et al. "In Vitro Effects of Antimicrobial Agents on Planktonic and Biofilm Forms of *Staphylococcus lugdunensis* Clinical Isolates." Antimicrobial Agents and Chemotherapy, March 2007, p. 888-895). Thus, the lethal dosage for treatment of biofilm forming microorganisms may be significantly higher than the standard therapeutically effective amount determined for planktonic microorganisms (i.e., a lethal amount or a lethal dosage) typically used by one of ordinary skill in the art or the amount approved by a regulatory agency (i.e., the FDA or its European counterpart).

Without wishing to be bound by theory, the surface active agent used in the context of the compositions of the invention, with or without additional agents, may penetrate and/or disrupt established biofilms by weakening or dispersing the polymer matrix or portions of the polymer matrix thereby diminishing or eliminating its function in providing resilience to the entrenched microorganisms. By weakening or disrupting of the polymer matrix of the biofilm, the surface active agent may enable the therapeutic agent to access the microorganisms of the biofilm and/or the tissues/surfaces beneath the biofilm improving delivery of a therapeutic agent to the microorganisms and/or the injured tissues.

Using this rationale, it would be expected that the amount of antimicrobial agent necessary to treat biofilm forming microorganisms when administered in conjunction with a surface active agent would be consistent with the standard therapeutically effective amount. Thus, the skilled artisan would expect to use a "standard therapeutically effective amount" or a "standard therapeutic dose" which as used herein refers to an amount of an antimicrobial agent suggested by the manufacturer or approved for clinical use by regulatory agencies such as, for example, the Food and Drug Administration (the "FDA") which effects treatment of microorganisms in planktonic form. A "standard therapeutic amount" or "standard therapeutic dose" may also refer to an amount of an agent sufficient to reduce or eliminate planktonic microorganisms. As described above, biofilms are generally not effected by antimicrobial agents provided at a standard therapeutic effective amount because biofilms are resistant to many antimicrobial agents. Therefore, a standard therapeutically effective amount may not represent a therapeutically effective amount of an antimicrobial agent when the antimicrobial agent is used to treat a biofilm. However, the data provided herein surprisingly demonstrate that a standard therapeutically effective amount of antimicrobial agent may be sufficient to effectively treat both planktonic biofilm forming microorganisms and preformed biofilms when the microbial agent is administered in combination with a surface active agent. Moreover, these data may additionally show that the amount of a microbial agent required to successfully treat biofilm forming microorganism when administered in combination with a surface active agent may be a "sub-lethal" amount (i.e., less than a standard therapeutically effective amount).

As used herein the terms "sub-lethal dose" or "sub-lethal amount" refer to an amount of an antimicrobial agent that is less than the standard therapeutically effective amount. In the context of the invention described herein, a sub-lethal amount of an antimicrobial agent may effectively eradicate or inhibit the growth of biofilm forming microorganisms or pathogens, or inhibit biofilm formation or eradicate formed biofilms. For example, a sub-lethal amount of an antimicrobial agent in some embodiments may be from about 10% to greater than about 50% less than the standard therapeutically effective amount or 10%, 15%, 20%, 25%, 30%, 35%, 40%, 45% or 50% less than the standard therapeutically effective amount approved by a regulatory agency. In other embodiments, a sub-lethal amount may be greater than 50% less than the standard therapeutically effective amount. In still other embodiments, a sub-lethal may include 100% of the standard therapeutically effective amount when the composition is used to treat a biofilm.

For example, a standard therapeutically effective amount of a silver sulfadiazine is about 1.0% by weight when used in an antimicrobial cream or gel. However, when silver sulfadiazine is administered in combination with a surface active agent to a biofilm forming microorganism, the amount of silver sulfadiazine in the composition may be decreased below the standard therapeutically effective amount to, for example, less than 1.0% by weight. Therefore, a sub-lethal amount of silver sulfadiazine in some embodiments, may be less than 0.95% by weight, less than 0.90% by weight, less than 0.85% by weight, less than 0.80% by weight, less than 0.75% by weight, less than 0.70% by weight, less than 0.65% by weight, less than 0.60% by weight or less than 0.55% by weight of the composition. In other embodiments, the amount of silver sulfadiazine may be less than 0.5% by weight of the composition. In embodiments, where silver sulfadiazine is used to treat a formed biofilm, a therapeutically effective amount may be 100% of a therapeutically effective amount or 1.0% by weight of the composition.

In another exemplary embodiment, a standard therapeutic dose of Polymyxin B is about 10,000 units/gram in various compositions. Thus, a "sub-lethal" dose or amount of Polymyxin B may be from about 1% to about 50% less than the about 10,000 units/gram standard therapeutic dose, or 9,900 units/gram to 5,000 units/gram, respectively. In certain embodiments, a sub-lethal amount may be greater than 50% less than a standard therapeutic effective amount, for example, about 60% less, about 70% less or about 80% less. In embodiments where a Polymyxin B is used to treat a formed biofilm, a therapeutically effective amount may be 100% of a therapeutically effective amount or 10,000 units/gram.

Similarly, a standard therapeutic dose of nystatin is about 4,000 units/gram. Thus, a "sub-lethal" dose of nystatin may be from about 1% less (3,960 units/gram) to about 50% less (2,000 units/gram). In yet another example, a standard therapeutically effective amount of nitrofurantoin is about 0.3%. Therefore, a sub-lethal amount of nitrofurantoin may be less than about 0.3%, for example, about 0.29% to about 0.15%. In embodiments where a Polymyxin B is used to treat a formed biofilm, a therapeutically effective amount may be 100% of a therapeutically effective amount or 4,000 units/gram.

The compositions of embodiments of the invention may be administered in combination with secondary active agents, such as, for example, drugs, adjuvants, protease inhibitors or other compatible drugs or compounds where such combination is seen to be desirable or advantageous in achieving the desired effects of the methods described herein. In some embodiments, the secondary active agent may be administered separately from the composition, and in others, the secondary active agent may be a component of the compositions of the invention. For example, in certain embodiments, the composition containing a surface active agent and a sub-lethal amount of an antimicrobial agent may further contain a drug for reducing irritation or enhancing healing such as, for example, an anti-inflammatory agent, anesthetic, pain killer or steroid.

Other embodiments of compositions encompassed by the invention may include additives such as stabilizers, antioxidants, osmolality adjusting agents, buffers, pH adjusting agents, chelants, calcium chelate complexes, salts or combinations thereof. For example, in some embodiments, a stabilizer such as appropriate pharmaceutical grade surfactants such as, TWEEN or saccharides, like dextrose, may be added to the compositions of the invention, and in some embodiments, such compositions may also include conventional pharmaceutical excipients and/or additives. For example, suitable pharmaceutical excipients may include stabilizers, antioxidants, osmolality adjusting agents, buffers, and pH adjusting agents, and suitable additives may include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or optionally, additions of calcium or sodium salts (for example, calcium chloride, calcium ascorbate, calcium gluconate or calcium lactate). Conventional nontoxic carriers may also be incorporated into such compositions and may include, for example, pharmaceutical grades of mannitol, lactose, starch, magnesium stearate, sodium saccharin, talcum, cellulose, glucose, sucrose, magnesium carbonate and the like. For example, about 1 to about 95% by volume or, in a further example, 25% to about 75% by volume of any of the carriers and excipients listed above may be mixed into the compositions of the invention. Additional additives such as coloring agents, thickeners, lubricants and so on may also be added to the compositions of the invention. Compositions of various embodiments of the invention may be prepared as described in Remington's Pharmaceutical Science, 17th ed., Mack Publishing Company, Easton, Pa. (1985), the entire disclosure of which is herein incorporated by reference, and such pharmaceutical compositions may be packaged for use as a liquid, gel, cream, solid, emulsion and dispersion.

Various embodiments of the invention also include methods for using the compositions described above. For example, some embodiments of the invention are directed to a method for treating a biofilm including the step of contacting the biofilm with a composition containing a surface active agent and a sub-lethal amount of an antimicrobial agent, and other embodiments include a method for preventing a biofilm including the step of contacting biofilm forming microorganisms with a composition containing a surface active agent and a sub-lethal amount of an antimicrobial agent. In some such embodiments, the biofilm may be present on a patient, for example, a human or a non-human animal, and in particular embodiments, the biofilm may be part of a wound. In other such embodiments, the biofilm or biofilm forming microorganisms may be present on a biomaterial that may contact a patient. In still other such embodiments, the biofilm or biofilm forming microorganisms may be present on tissue removed from a patient or tissue that is outside of the patient and may or may not be replaced back into the patient.

The invention also encompasses methods for using a composition including a surface active agent and a sub-lethal amount of a antimicrobial agent for treating surfaces. Therefore, the compositions of the invention may have non-pharmaceutical applications. For example, in some embodiments, a composition including a surface active agent and a sub-lethal amount of an antimicrobial agent may by applied to an inanimate object, such as, but not limited to a chair, table, side board, machine or various parts of a machine or combinations thereof. In other embodiments, the compositions of the invention may be applied surgical instruments and/or surfaces of objects in an operating room. In still other embodiments, the compositions of the invention may be applied to surfaces of devices meant to be implanted in a patient prior to implantation such as, a medical device, for example, a catheter.

In embodiments such as those described above, contacting the biofilm or the biofilm forming microorganism may occur by any method known in the art. For example, in some embodiments, the composition may be applied by hand or mechanically using, for example, extrusion or spray delivery. In the context of embodiments that include contacting biofilms or biofilm forming microorganisms present on a patient, the composition may be delivered by, for example, topical administration which may be performed by hand, mechanically (e.g., extrusion and spray delivery) or as a component in a dressing such as gauze or other wound coverings.

In embodiments in which the compositions of the invention are administered or applied directly to a tissue or biomaterial surface by hand or mechanically, it may be important to apply the composition so as to achieve a therapeutic coating. A therapeutic coating generally refers to an amount of the composition which may form a substantially uniform covering over the effected area and may encompass non-effected areas surrounding an injury or wound. In embodiments in which the composition is delivered by hand, there can be considerable variation in the thickness of layers applied by practitioners. In some embodiments, a therapeutic coating may be applied or administered alone, and in other embodiments, a therapeutic coating may be applied in combination with an overlying dressing. In embodiments in which the composition is applied or administered mechanically using a device that physically pushes (i.e., extrusion) or sprays the composition onto a tissue or biomaterial surface, a uniform therapeutic coating may be achieved in a single administration or in several applications over the effected area, and a therapeutic coating delivered in this manner may be provided alone or in combination with an overlying dressing.

The thickness of a therapeutic coating of the composition when applied may vary in accordance with the size of a wound, the time available to apply the composition, the amount of composition available and other variables. For example, in various embodiments, the thickness of the applied compositions may be from about 1 inch thick to less than about $1/10,000$ inch thick or about 1 inch, about $1/2$ inch, about $1/4$ inch or about $1/100$ inch. In some embodiments, the thickness may vary in a single application. For example, the composition may be applied more thickly in the area of a wound and less thickly in the area surrounding the wound. In other embodiments, less composition may be applied to a wound that does not exhibit signs of biofilm formation while in still other embodiments, a greater amount of the composition may be applied to wounds that exhibit symptoms of biofilm formation. In yet other embodiments, a wound and the area surrounding the wound may be covered with a medical fabric such as, for example, band-aids or gauze, after being contacted with the composition.

The methods described above may be useful for treating patients exhibiting a number of indications or suffering from any number of conditions that may be susceptible to microbial biofilm formation or may already have a biofilm present. Such patients may be considered "in need of treatment." In some embodiments, the indications or conditions that may include risk of biofilm formation and may require treatment using the compositions of the invention may arise from, for example, injury in which skin and/or skin function is disrupted or surgery. Examples of such injuries may include, but are not limited to burns, abrasions, cuts, scrapes, and other denuding tissue injuries or combinations of these. In other embodiments, the compositions of the invention may be used to treat chronic wounds. In general, chronic wounds are characterized by non-healing skin wounds and include, for example, chronic venous ulcers, diabetic ulcers, arterial ulcers, pressure ulcers (e.g., decubitis ulcers), radiation ulcers, traumatic wounds, open, complicated non-healing wounds and the like.

Still other embodiments of the invention include methods for treating or preventing a microbial biofilm including the steps of: administering a first composition containing a surface active agent and that does not contain an antimicrobial agent; and administering a second composition that contains a surface active agent and a sub-lethal amount of an antimicrobial agent. In such embodiments, the second composition may generally be administered after the first composition. In some embodiments, the first composition may be applied and the second composition may be applied without any intervening steps, and in other embodiments, the first composition may be applied and then removed or partially removed by, for example, being wiped away prior to administration of the second composition, prior to administration of the second composition. In still other embodiments, the method may further include the step of applying a dressing or covering to the treated surface following administration of either the first or second or both compositions. In yet another embodiment, the second composition may be included in the dressing material. For example, the second composition may be impregnated in a dressing material or otherwise contained or encompassed by the dressing material. In such embodiments, the dressing including the second composition may be applied over a surface to which the first composition has been administered. In an alternative embodiment, the second composition may be applied directly to a dressing material by, for example, coating a surface of the dressing material with the second composition, prior to applying the dressing to the surface treated with the first composition.

The time between the first administration and the second administration may vary throughout embodiments and may be based on the patient and practitioner. For example, in various embodiments, the time between administration of the first and second compositions may be from a partial second (e.g., 0.001 seconds) up to several minutes (e.g., 1, 2, 3, 4, 5, 10, 15, 20, 25 or 30 or greater than 30 minutes) or several hours (e.g., 1, 2, 3, 4 or 5 or greater than 5 hours).

Yet other embodiments of the invention include a dressing for treating or preventing a microbial biofilm that includes: a first layer including a composition containing a surface active agent and no antimicrobial agent; a second layer including a second composition containing a surface active agent and a sub-lethal amount of an antimicrobial agent; and a dressing material supporting the first and second composition layers. In such embodiments the second layer is located between the first layer and the dressing material. In some embodiments, the second layer may form a coating covering a surface of the dressing material, and in other embodiments, the second layer is impregnated or otherwise contained within or encompassed by the dressing material. In certain embodiments, the first and second composition layers may completely encompass the dressing, and in others, the first and/or second composition layers may be placed such that the compositions may be positioned to be delivered to only a portion of the patient to which the dressing is applied. For example, in one embodiment, the entire dressing includes the first and second composition layers, and in another embodiment, the dressing may include a middle section that includes first and second composition layers that is flanked on either side by portions of the dressing that do not contain composition layers. In still another embodiment, the entire dressing may contain a first composition layer and a portion of the dressing may contain the second composition layer.

In still other embodiments, the dressing may further include a spacer layer between the first and second composition layers. In some embodiments, the spacer layer may be a dressing material that allows the antimicrobial agent to be brought into contact with the patient after the dressing has been applied to the patient. In other embodiments, the spacer layer may be a pharmaceutical agent such as, for example, a polymer, a cream, a wax and the like that may separate the first and second compositions. In certain embodiments, the spacer layer may lose its integrity by, for example, disintegrating, dissipating, becoming porous, etc., upon application of the dressing to a patient. For example, in one embodiment, the spacer layer may degrade as it is warmed to body temperature. In general as the spacer layer loses integrity means, it may no longer function as a barrier between the first and second composition. Thus, the second composition may come into contact with patient and/or the first composition as the spacer layer loses integrity.

The dressing material of embodiment may be any pharmaceutically acceptable fabric. For example, in various embodiments, the dressing material may be gauze, a gauze pad, polymeric or natural fiber band-aid, second skin or any other type of material or fabric useful in the medical arts to cover a wound or at least keep a therapeutic agent or pharmaceutical composition in contact with a patient.

The compositions of the invention may be packaged in any way which allows a practitioner or an injured individual access to the composition following injury. For example, in one embodiment, the first and/or second compositions are contained within a tube or bottle from which the composition may be poured and applied to the injury, and in another embodiment, the first and/or second composition may be absorbed onto a swab which may be used to apply the compositions of the invention. In still another embodiment, the first and/or second composition may be contained within a vial that is broken to release the composition which may then be applied by means discussed herein above. Of course, other packaging means are available and may be used in conjunction with embodiments of the invention.

Various embodiments of the invention described above may prevent biofilm formation. In such embodiments, the patient or wound may not exhibit signs or symptoms of biofilm infestation. However, microorganisms with the potential to form a biofilm may be present on the patient or within the wound itself. The compositions of the invention may eliminate the biofilm forming microorganisms before biofilm formation has if the composition is applied to a wound prior to formation of a biofilm. As described above, biofilm forming microorganisms begin to form a biofilm only when a population of planktonic microorganisms reach a specific cell density and/or when the concentration of microorganism produced autoinducer has reached a threshold level. The concentration of autoinducer and cell density requirements may vary among biofilm forming species. Without wishing to be bound by theory, application of the compositions of the invention prior to formation of a biofilm may reduce the microorganism population such that planktonic microorganisms may not reach an adequate cell density to form a biofilm thereby inhibiting biofilm formation.

Because biofilms may form rapidly, it may be advantageous for emergency personnel (i.e., first responders) to apply a composition according to the present invention at the scene of the injury. Thus, in another embodiment, the present invention provides a method for treating a wounded patient by administering to the wounded patient a composition containing a surface active agent and a sub-lethal amount of an antimicrobial agent within about 10 hours of injury. In other embodiments, the wound may be treated within less than 10 hours. For example, a wound may be treated within 8 hours, 5 hours, 4, hours, 3 hours, 2 hours or 1 hour or within 30 minutes, within 10 minutes or within 5 minutes. Without wishing to be bound by theory, treating an injury within about 2 hours or less may ensure that the wound is treated while the biofilm forming pathogens in the wound are in a planktonic state or before biofilm forming pathogens have invaded the wound. Thus, any biofilm forming pathogens are contacted by the composition of the invention before the concentration of autoinducer has reached a threshold level to induce biofilm formation and/or before the cell density of the pathogen has reached a similar threshold level. Accordingly, formation of a biofilm may be reduced or eliminated, and the wound may be more easily treated.

The present invention may be embodied in other specific forms without departing from the spirit or essential attributes thereof. This invention encompasses all combinations of the different aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

This invention and embodiments illustrating the method and materials used may be further understood by reference to the following non-limiting examples.

EXAMPLES

Overview

Compositions prepared in accordance with embodiments of the invention were evaluated for efficacy using "The Calgary Biofilm Device" as described in Ceri et al. "The Calgary Device: New Technology for the Rapid Determination of Antibiotic Susceptibilities of Bacterial Biofilms." J. Clin. Microbio. 1999; 37:1771-1776 hereby incorporated by reference in its entirety. Briefly, this simple assay allows microorganisms to grow on pins which are positioned on the lid of a 96 well microtiter plate and which protrude into the wells of the 96 well microtiter plate when the lid is positioned on the plate. Biofilm forming microorganisms are placed on the pins and contact growth media and/or test compounds in the wells of a microtiter plate. This allows rapid analysis of test compounds efficacy against biofilm forming microorganisms. The data resulting from the assay produces both MIC and MBEC values by observing biofilm growing on the pegs. Similar assays may also be used to determine the MIC and MBEC of planktonic microorganisms by growing the microorganisms suspended in the wells of a 96 well microtiter plate, and observing the growth of the microorganisms in wells that contain the test compound and comparing these values with control well that do not contain a test compound.

The assay described above compounds according to various embodiments of the invention were tested against biofilm forming microorganisms: *Pseudomonas aeruginosa* (ATCC 27853), *Staphylococcus aureus* (ATCC 29213), and *Staphylococcus epidermidis* (ATCC 35984). These microorganisms were grown in media containing various compositions of the invention including:

Poloxamer 188 dissolved in water to concentrations of 45%, 50% and 55% by volume poloxamer 188.

PSSD (50% poloxamer 188 and 1% silver sulfadiazine in water) at 100% and diluted with 50% poloxamer 188 in water to concentrations of 90%, 80%, 70%, 60% and 50% by volume PSSD.

PTAG (50% poloxamer 188 and TAG (Polymyxin B [10,000 U/g], nitrofurantoin [0.3%], nystatin [4,000 U/g]) in water) at 100% and diluted with 50% poloxamer 188 in water to concentrations of 90%, 80%, 70%, 60% and 50% by volume PTAG.

SSD cream (1% silver sulfadiazine) at 100% and diluted in cream to concentrations of 90%, 80%, 70%, 60% and 50% by volume SSD.

The results provided below show that all of compounds of the invention tested had some degree of antimicrobial biofilm activity and various tested compounds of the invention were able to both prevent biofilm formation and eradicate preformed biofilms. Generally, this activity is improved over the activity of silver sulfadiazine observed in side-by-side comparisons.

Inhibition of Preformed Biofilms

An inoculum of the microorganism to be tested was prepared to match a 0.5 McFarland Standard ($1.5 \times 10^8$ cells per ml) in 3 ml of sterile water in a glass test tube using a sterile cotton swab. This inoculum was then diluted 1 in 30 in Cation Adjusted Mueller Hinton Broth (CAMHB) and inverted 3-5 times to achieve uniform mixing of the microorganism. A sample (100 µl) of the diluted inoculum was serially diluting and spot plating on TSA to confirm the cell density of the sample. 150 µl of the remaining diluted inoculum was then placed in each well of a 96 well NUNC bottom microtiter plate, and a lid including 96 pegs was placed on the plate. The device (i.e., the microtiter plate and corresponding peg containing lid) was placed on a shaker in a humidified incubator at 37° C. for 24 hours set at 110 revolutions per minute to allow biofilm on the peg.

Following incubation, the lid was removed from the device and the pegs were rinsed in sterile saline to remove planktonic cells from the biofilm that formed on the plate. The peg containing lid was then transferred to challenge plate, and the challenge plate was incubated at 37° C. for a specified contact time. A contact plate is a sterile 96-well microtiter plate whose wells contain a concentration of the test composition as specified above.

Surviving biofilm forming microorganisms were recovered by rinsing the pegs in 0.9% sterile saline and then transferring the pegs to a recovery media which was then sonicated to dislodge surviving biofilm forming bacteria from the peg. The recovery plate was then incubated for 24 hours at 37° C., and the cell density was determined by obtaining an optical density at 630 nm ($OD_{630}$). In the tables below, clear wells having an $OD_{630}$ less than 0.1 are evidence that the biofilm forming bacteria were eradicated and denoted by a minus (−). Wells in which bacterial growth is evident ($OD_{630}$ greater than 0.1) are denoted with a plus (+).

Inhibition of Biofilm Formation

A inoculum as described above were prepared, diluted 1 in 30 in Cation Adjusted Mueller Hinton Broth (CAMHB), inverted 3-5 times to achieve uniform mixing of the microorganism and sample (100 µl) of the diluted inoculum was serially diluting and spot plating on TSA to confirm the cell density of the sample. A challenge plate was prepared as described above, and 20 µl of the inoculum was added to each well of the challenge plate. A sterile lid having 96 pegs corresponding to each of the wells of the challenge plate was placed over the challenge plate and the device was incubated in a humidified incubator at 37° C. for 24 hours shaking at 110 revolutions per minute to allow biofilm on the peg for a specified contact time. The plate was then removed from incubation, and surviving biofilm forming bacteria on each peg were recovered as described above. Following incubation, the cell density was determined by obtaining an optical density at 630 nm ($OD_{630}$). In the tables below, clear wells having an $OD_{630}$ less than 0.1 are evidence that the biofilm forming bacteria were eradicated and denoted by a minus (−). Wells in which bacterial growth is evident ($OD_{630}$ greater than 0.1) are denoted with a plus (+).

MBC and MBEC

The minimum bactericidal concentration (MBC) value represents the lowest concentration which kills 99.9% of the population. Results were determined following the 24 hour incubation from the Test panels using the plate reader. To determine MBC, the optical density of the wells of each challenge plate was determined at 630 nm ($OD_{630}$). Clear wells ($OD_{630}$<0.1) are evidence of inhibition and denoted (−). Wells in which bacterial growth is evident ($OD_{630}$ greater than 0.1) are denoted with a plus (+).

The minimum biofilm eradication concentration (MBEC) was determined following the 24 hour incubation from the MBEC panels using the plate reader in conjunction with Log 10 reduction data. To determine MBEC, the optical density of the wells of the recovery plate was determined at 630 nm ($OD_{630}$). Clear wells ($OD_{630}$<0.1) are evidence of biofilm eradication and denoted (−). The MBEC is defined as the minimum concentration of antibiotic that inhibits growth of the biofilm. Wells in which bacterial growth is evident ($OD_{630}$ greater than 0.1) are denoted with a plus (+).

Example 1

*P. aeruginosa*

An inoculum of *P. aeruginosa* was prepared as described above and tested in an inhibition of biofilm assay to yield the following results:

| MBC | 55% | 50% | 45% | | | |
|---|---|---|---|---|---|---|
| P. 188 | − | − | + | | | |
| | 100% | 90% | 80% | 70% | 60% | 50% |
| PSSD | − | − | − | − | − | − |
| TAG | − | − | − | − | − | − |
| SSD | − | − | − | − | − | − |

| MBEC | 55% | 50% | 45% | | | |
|---|---|---|---|---|---|---|
| P. 188 | − | − | + | | | |
| | 100% | 90% | 80% | 70% | 60% | 50% |
| PSSD | + | − | + | + | − | − |
| TAG | − | − | + | − | + | − |
| SSD | + | + | − | + | − | + |

An inoculum of *P. aeroginosa* was prepared as described above and tested in an inhibition of preformed biofilm assay to yield the following results:

| MBC | 55% | 50% | 45% | 100% | 90% | 80% | 70% | 60% | 50% |
|---|---|---|---|---|---|---|---|---|---|
| P. 188 | − | − | + | | | | | | |
| PSSD | | | | − | − | − | − | − | − |
| TAG | | | | − | − | − | − | − | − |
| SSD | | | | − | − | − | + | − | − |

| MBEC | 55% | 50% | 45% | 100% | 90% | 80% | 70% | 60% | 50% |
|---|---|---|---|---|---|---|---|---|---|
| P. 188 | − | + | + | | | | | | |
| PSSD | | | | + | − | + | + | + | − |
| TAG | | | | + | + | + | + | + | + |
| SSD | | | | + | + | + | + | + | + |

Example 2

*S. aureus*

An inoculum of *S. aureus* was prepared as described above and tested in a inhibition of biofilm assay to yield the following results:

| MBC | 55% | 50% | 45% | 100% | 90% | 80% | 70% | 60% | 50% |
|---|---|---|---|---|---|---|---|---|---|
| P. 188 | − | + | + | | | | | | |
| PSSD | | | | − | − | − | − | − | − |
| TAG | | | | − | − | − | − | − | − |
| SSD | | | | + | + | + | + | − | − |

| MBEC | 55% | 50% | 45% | 100% | 90% | 80% | 70% | 60% | 50% |
|---|---|---|---|---|---|---|---|---|---|
| P. 188 | + | + | + | | | | | | |
| PSSD | | | | − | − | + | + | + | − |
| TAG | | | | + | − | + | − | − | − |
| SSD | | | | + | + | + | + | + | + |

An inoculum of *S. aureus* was prepared as described above and tested in an inhibition of preformed biofilm assay to yield the following results:

| MBC | 55% | 50% | 45% | 100% | 90% | 80% | 70% | 60% | 50% |
|---|---|---|---|---|---|---|---|---|---|
| P. 188 | − | + | + | | | | | | |
| PSSD | | | | − | − | − | − | − | − |
| TAG | | | | − | − | − | − | − | − |
| SSD | | | | + | + | + | + | − | − |

| MBEC | 55% | 50% | 45% | 100% | 90% | 80% | 70% | 60% | 50% |
|---|---|---|---|---|---|---|---|---|---|
| P. 188 | + | + | + | | | | | | |
| PSSD | | | | + | − | + | + | + | − |
| TAG | | | | + | − | + | + | + | + |
| SSD | | | | + | + | + | − | − | − |

Example 3

*S. epidermidis*

An inoculum of *S. epidermidis* was prepared as described above and tested in a inhibition of biofilm assay to yield the following results:

| MBC | 55% | 50% | 45% | 100% | 90% | 80% | 70% | 60% | 50% |
|---|---|---|---|---|---|---|---|---|---|
| P. 188 | + | + | + | | | | | | |
| PSSD | | | | − | − | − | − | − | − |
| TAG | | | | − | − | − | − | − | − |
| SSD | | | | + | + | + | + | + | + |

| MBEC | 55% | 50% | 45% | 100% | 90% | 80% | 70% | 60% | 50% |
|---|---|---|---|---|---|---|---|---|---|
| P. 188 | − | + | + | | | | | | |
| PSSD | | | | − | − | + | + | + | − |
| TAG | | | | + | − | − | − | − | − |
| SSD | | | | + | + | + | + | + | + |

An inoculum of *S. epidermidis* was prepared as described above and tested in an inhibition of preformed biofilm assay to yield the following results:

| MBC | 55% | 50% | 45% | 100% | 90% | 80% | 70% | 60% | 50% |
|---|---|---|---|---|---|---|---|---|---|
| P. 188 | + | + | + | | | | | | |
| PSSD | | | | − | − | − | − | − | − |
| TAG | | | | − | − | − | − | − | − |
| SSD | | | | + | + | + | + | + | + |

| MBEC | 55% | 50% | 45% | 100% | 90% | 80% | 70% | 60% | 50% |
|---|---|---|---|---|---|---|---|---|---|
| P. 188 | − | − | + | | | | | | |
| PSSD | | | | + | − | + | + | + | + |
| TAG | | | | + | − | + | − | + | − |
| SSD | | | | + | + | + | + | + | + |

What is claimed is:

1. A method for treating a microbial biofilm on a patient comprising contacting the microbial biofilm with a composition comprising about 20 w/w % to about 90 w/w % of a surface active agent selected from the group consisting of poloxamer 127, poloxamer 188, poloxamer 237, poloxamer 335, poloxamer 407, and combinations thereof and about 10% to greater than 50% less than a standard therapeutically effective amount of an antimicrobial agent for treatment of biofilms.

2. The method of claim 1, wherein the antimicrobial agent is selected from the group consisting of antibacterial agents, antifungal agents, antiviral agents, and combinations thereof.

3. The method of claim 1, wherein the antimicrobial agent is selected from the group consisting of furaltadone, furazolium chloride, nifuradene, nifuratel, nifurfoline, nifurpirinol, nifurprazine, nifurtoinol, nitrofurantoin, furazolidone, 2-(methoxymethyl)-5-nitrofuran, nidroxyzone, nifuroxime, nifurazide, nitrofurazone, nystatin, polymyxin, silver sulfadiazine, nanocrystalline silver, ionic silver, honey, iodine, benzalkonium chloride, alcohol, hydrogen peroxide, chlorhexidine, and combinations thereof.

4. The method of claim 1, wherein the amount of an antimicrobial agent is less than about 1% by weight of the composition.

5. The method of claim 1, wherein the amount of an antimicrobial agent is less than about 0.95% by weight of the composition.

6. The method of claim 1, wherein the amount of an antimicrobial agent is less than about 0.75% by weight of the composition.

7. The method of claim 1, wherein the surface active agent is poloxamer 188.

8. The method of claim 1, wherein contacting the microbial biofilm comprises applying the composition to a wound.

9. The method of claim 1, wherein contacting the microbial biofilm comprises administering the composition topically.

10. The method of claim 9, wherein administering the composition topically is selected from the group consisting of administering by hand, administering by an extruder, spray delivery, applying a dressing including the composition, and combinations thereof.

11. The method of claim 1, wherein contacting the microbial biofilm comprises contacting tissue from the patient that is outside the patient.

12. The method of claim 1, wherein contacting the microbial biofilm comprises applying the composition to a dressing and applying the dressing to the patient.

13. The method of claim 1, wherein the patient is afflicted with an injury.

14. The method of claim 13, wherein the injury is selected from the group consisting of burns, abrasions, cuts, scrapes, denuding tissue injuries, and combinations thereof.

15. The method of claim 1, wherein the patient is afflicted with a chronic wound.

16. The method of claim 15, wherein chronic wound is selected from the group consisting of venous ulcers, diabetic ulcers, arterial ulcers, pressure ulcers, radiation ulcers, traumatic wounds, non-healing wounds, and combinations thereof.

* * * * *